(12) United States Patent
Nies

(10) Patent No.: US 9,764,057 B2
(45) Date of Patent: Sep. 19, 2017

(54) HYDRAULIC CEMENT-BASED IMPLANT MATERIAL AND USE THEREOF

(75) Inventor: Berthold Nies, Fränkisch-Crumbach (DE)

(73) Assignee: InnoTERE GmbH, Dresden (DE)

( * ) Notice: Subject to any disclaimer, the term of this patent is extended or adjusted under 35 U.S.C. 154(b) by 1107 days.

(21) Appl. No.: 12/663,052

(22) PCT Filed: Jun. 6, 2008

(86) PCT No.: PCT/EP2008/057099
§ 371 (c)(1),
(2), (4) Date: May 31, 2010

(87) PCT Pub. No.: WO2008/148878
PCT Pub. Date: Dec. 11, 2008

(65) Prior Publication Data
US 2012/0191214 A1    Jul. 26, 2012

(30) Foreign Application Priority Data
Jun. 6, 2007   (DE) .................. 10 2007 027 511

(51) Int. Cl.
| | |
|---|---|
| A61L 24/02 | (2006.01) |
| A61L 24/00 | (2006.01) |
| A61L 27/40 | (2006.01) |
| A61K 6/00 | (2006.01) |
| A61K 6/06 | (2006.01) |

(52) U.S. Cl.
CPC ........ *A61L 24/0084* (2013.01); *A61K 6/0008* (2013.01); *A61K 6/0067* (2013.01); *A61K 6/0643* (2013.01); *A61K 6/0675* (2013.01); *A61L 24/02* (2013.01); *A61L 27/40* (2013.01); *A61L 2430/02* (2013.01)

(58) Field of Classification Search
CPC ...... A61K 6/033; A61K 6/007; A61K 6/0073; A61K 6/0082; A61K 6/0002
USPC ...................................................... 523/115
See application file for complete search history.

(56) References Cited

U.S. PATENT DOCUMENTS

| | | | |
|---|---|---|---|
| 5,262,166 A | 11/1993 | Liu et al. | |
| 5,336,264 A | 8/1994 | Constanz et al. | |
| 6,117,456 A | 9/2000 | Lee et al. | |
| 6,420,454 B1 | 7/2002 | Wenz et al. | |
| 6,495,156 B2 | 12/2002 | Wenz et al. | |
| 6,642,285 B1 | 11/2003 | Bohner | |
| 7,709,029 B2 | 5/2010 | Chow et al. | |
| 2002/0166480 A1 | 11/2002 | Zimmerman | |
| 2003/0161858 A1* | 8/2003 | Lidgren ................. | 424/423 |
| 2004/0244651 A1 | 12/2004 | Lemaitre et al. | |
| 2005/0074415 A1 | 4/2005 | Chow et al. | |
| 2005/0111300 A1 | 5/2005 | Nies et al. | |
| 2005/0208094 A1* | 9/2005 | Armitage ............... | A61K 31/74 424/423 |
| 2005/0251149 A1* | 11/2005 | Wenz .......................... | 606/94 |
| 2006/0041033 A1* | 2/2006 | Bisig et al. ................. | 523/116 |

FOREIGN PATENT DOCUMENTS

| | | |
|---|---|---|
| CN | 1821143 A | 8/2006 |
| DE | 19858891 A1 | 6/2000 |
| EP | 1 302 453 A1 | 4/2003 |
| EP | 1296909 B1 | 4/2003 |
| EP | 1520562 A2 | 4/2005 |
| JP | S61246108 A | 11/1986 |
| JP | 1111762 A | 4/1989 |
| JP | 1139516 A | 6/1989 |
| WO | 96/39202 A | 12/1996 |
| WO | 01/76649 A1 | 10/2001 |
| WO | 02/062721 A1 | 8/2002 |
| WO | 2004/0937834 A2 | 11/2004 |
| WO | 2005/069837 A2 | 8/2005 |

(Continued)

OTHER PUBLICATIONS

Kolliphor EL technical data sheet; BASF; Mar. 2012.*
Kolliphor EL MSDS; Sigma-Aldrich; May 29, 2012.*
Takagi S. et al: Premixed Calcium Phosphate Cement Pastes; Sixth World Biomaterials Congress Transactions; 2000.
Carey L. E. et al: Premixed Rapid-Setting Calcium Phosphate Composites for Bone Repair; Biomaterials 26 (2005) 5002-5014.
Schwardt et al: Kyphos FS™ Calcium Phosphate for Balloon Kyphoplasty: Verification of Compressive Strength and Instructions for Use; European Cells and Materials vol. 11, suppl. 1. 2006, p. 28.
Brown W E et al: A new calcium phosphate water setting cement. In: Brown PW, editor. Cements research progress. Westerville, OH: American Ceramic Society; 1986; pp. 352-379.

(Continued)

*Primary Examiner* — Michael Pepitone
(74) *Attorney, Agent, or Firm* — FisherBroyles, LLP; Andrew K. Gonsalves, Esq.

(57) ABSTRACT

The invention relates to implant materials that are based on hydraulic cements in the form of one or more pastes, suspensions or dispersions that contain mineral and/or organic and/or organomineral solids and that react, when combined or when reacted with an aqueous liquid, to a solid in a cement-type initiation reaction. The invention also relates to the use of these materials as technical, medical-technical and/or pharmaceutical products, especially as bone cements, bone replacement materials, bone glues, dental filling materials and implantable active ingredient carriers. The implant materials according to the invention in the form of one or more pastes, suspensions or dispersions that contain mineral and/or organic and/or organomineral solids are formulated in an excipient liquid in such a manner that the pastes, suspensions or dispersions are stable in storage at normal conditions over a prolonged period of time and that they react, when combined with an aqueous liquid or when added to an aqueous liquid, in a cement-type initiation reaction and set to a solid. The excipient liquid of the mineral paste, suspension or dispersion is substantially water-free, and water immiscible or insoluble or hardly soluble in water in the chemical sense.

25 Claims, No Drawings

(56) References Cited

FOREIGN PATENT DOCUMENTS

| WO | 2005/120595 A2 | 12/2005 |
|---|---|---|
| WO | 2006/014886 A2 | 2/2006 |
| WO | 2006/127989 A1 | 11/2006 |
| WO | 2008/037991 A1 | 4/2008 |

OTHER PUBLICATIONS

Bohner et al: Effect of several additives and their admixtures on the phisico-chemical properties of a calcium phosphate cement. J Mater Sci Mater Med 2000; 11 : 111-116.
Driessens et al: Effective formulations for the preparation of calcium phosphate bone cements. J Mater Sci Mater Med. 1994; 5: 164-170.
Dörfler H.-D.: Makro- und Mikroemulsionen in Grenzflächen und kolloid-disperse Systeme. Springer, Berlin, 2002, Chapter 13 (see specification p. 18, 1st paragraph).
Pittet et al: Mechanical characterization of brushite cements: A Mohr circles' approach, J Biomed Mater Res 2000; 53 (6) 769-780 (see specification p. 42, 3rd paragraph from the bottom).

* cited by examiner

HYDRAULIC CEMENT-BASED IMPLANT MATERIAL AND USE THEREOF

BACKGROUND OF THE INVENTION

The invention concerns implant materials on the basis of hydraulic cements in the form of one or several pastes, suspensions or dispersions containing mineral and/or organic and/or organo-mineral solids that upon combination or reaction with an aqueous liquid react in a cement-like curing reaction to a solid material as well as their use as technical, medical-engineering and/or pharmaceutical products, in particular as bone cements, bone replacement materials, bone adhesives, tooth filling materials and implantable carriers for active ingredients.

Mineral reactive systems have been in use for a long time in the form of various cements, plasters, etc. Typically, they are comprised of mineral powders that are mixed with water. These mixtures cure within minutes up to days and reach their final composition often only after days to months. The curing reaction is usually comprised of a dissolution of water-soluble powder components and subsequent precipitation of a more stable or less soluble phase or salt form, or in a recrystallization of meta-stable powder components to a modification that is more thermodynamically stable under the application conditions. Often, two or several water-soluble powder components react to a hardly soluble substance.

Mineral cements are seldomly used in pure form but contain usually large proportions of mineral or organic fillers and/or are reinforced by addition of organic, mineral or metallic fibers (or other reinforcement elements).

The prevalence of mineral reactive systems has greatly increased in the last decades and this despite the increase and spread of alternative materials such as metals, ceramics and plastic materials. An important reason for this is the great application-related diversification of the relatively minimal number of principally different reactive systems. This diversification is expressed primarily in the application-related preformulation of reactive components with fillers, reinforcement elements, substances that affect the flowability, adhesion, curing kinetics, frost resistance etc. Examples are, in addition to the classic Portland cement and gypsum, formulations that are already mixed with a suitable type and quantity of sand in accordance with their use as screed or plastering coat. Mixtures with different polymers (dissolved and/or dispersed) have opened further fields of application for the mineral reactive systems (for example, thin-bed adhesives for tile, injectable dowel compounds) that would not be realizable with purely mineral starting materials and have therefore created significant added value in industry.

In medicine (medical engineering) mineral cements have also been used more and more for some years now. First, they have been used as dental filling materials (for example, root fillings) and since approximately 1990 also as filling and reinforcement materials for bone defects in oral and maxillofacial surgery (OMF surgery) as well as orthopedics. Primarily in the medical field the use of mineral reactive systems is still at its beginnings, primarily because only a very limited number of substances is acceptable for use in the body and because very stringent requirements are placed on the products with respect to purity and quality. With respect to the starting materials, moreover many substances are not obtainable in the required quality and must therefore be specifically produced for these applications.

An additional hurdle for expanding the use of mineral reactive systems in medicine and technology is the typical admixture of powder and liquid. This is in any case of a complex nature and the quality of the result is based on the ability and care of the user. In case of medical applications, it is all the more difficult that the mineral cements that have been introduced so far in this field react very sensitively with respect to deviations of the powder/liquid ratio and the clinical users—in contrast to technical applications (e.g. in construction)—up to now have had little training and little experience (the existing long-term experience with polymer-based reactive systems—PMMA bone cement—is moreover rather impairing because the mineral reactive systems behave completely differently) in the preparation of the mineral reactive systems.

The attempts in regard to simplification of powder-liquid mixtures have not yet been successful. In medical technology primarily different mixing systems have been developed that reduce the variability caused by the user and increase the handling comfort for the user.

EP1520562 A2 discloses a device for mixing and dispensing liquid and powdery materials for medical use with a mixing cylinder and a perforated mixing piston that is axially and rotatably movable within the mixing cylinder by means of an actuating rod, with an axially movable dispensing piston and with a closable dispensing piston at the mixing cylinder. This patent application shows in an exemplary manner the apparatus-based expenditure that is proposed by a manufacturer of bone cements as a solution for the problems of powder/liquid mixture under surgery conditions. Basically, however this proposal (like that of many others) does not solve the problem but only compensates to a certain degree by increased apparatus-based expenditure. Moreover, in practice it has been found that despite complex apparatus structure, these devices in no way provide satisfactory results without intensive training and practice. An apparatus-based solution therefore can be eliminated.

U.S. 2004/244651 A1 discloses calcium phosphate cement composition of at least two reactive components in liquid or pasty form that as a carrier liquid contain exclusively water and/or aqueous solutions. The compositions of the exemplary mentioned cements are in line with conventional calcium phosphate cements but contain additional mineral components in order to stabilize the thus produced pastes. Any expert in the field of calcium phosphate cements will question whether one of the mentioned exemplary formulations of the described composition will have an extended shelf life. For the so-called meta-stable calcium phosphates—tetracalcium phosphate (TTCP), β-tricalcium phosphate (β-TCP), and α-tricalcium phosphate (α-TCP)— it holds true in any case that they are stable only under practically anhydrous conditions. All manufacturers of such cements therefore stress the need for manufacturing conditions and packaging that minimize access of water (or moisture in the air) to the cement powder.

S. Takagi, S. Hirayama, A. Sugawara and L. C. Chow disclose in their publication PREMIXED CALCIUM PHOSPHATE CEMENT PASTES (Sixth World Biomaterials Congress Transactions; 2000) experiments in regard to mixing different calcium phosphate cements with glycerine as a carrier liquid. After introduction of these preparations into aqueous solutions they react to solid materials that however have relatively minimal strength values and exhibit very long curing times. Glycerine is moreover a very hygroscopic substance that has the tendency to absorb water so that the shelf life is limited. This problem applies in principle to all liquids that are miscible in the chemical sense with water that, moreover, in most cases can be made anhydrous only with great expenditure. The same group of authors disclose in a newer publication (Premixed rapid setting calcium phosphate composites for bone repair; Carey, Xu, Simson, Takagi, Chow in Biomaterials 26 (2005) 5002-5014) formulations that have been further developed and that employ also water-soluble carrier liquids and compensate some of the aforementioned disadvantages by modifications of the composition. The disadvantages of potentially minimal shelf life and the lack of universal applicability onto the various reactive organo-mineral reactive systems remains however untouched thereby.

WO 2002/062721 A1 and WO 2004/093734 A2 disclose a premixed calcium phosphate cement paste of a mixture of glycerine as a carrier liquid and a calcium phosphate with different additives that, in contact with aqueous solutions, cure to a solid material. This formulation is supposed to reduce the aforementioned disadvantages of the cement paste of calcium phosphates and glycerine by addition of acids and gel forming agents and in particular lead to shorter curing times and improved paste cohesion. The principal disadvantage of cement pastes that are based on water-soluble carrier liquids (see above) is however not eliminated thereby. The additives are able to compensate them only partially. A universally applicable method and composition for producing a paste-based (bone) cement with extended shelf life is not possible therewith. U.S. Pat. No. 6,642,285 B1 discloses a calcium phosphate cement composition that contains a hydrophobic liquid. Accordingly, first calcium phosphate powder is mixed with the appropriate aqueous mixing solutions and the resulting pastes are mixed then with oils in order to obtain, with addition of emulsifying agents and as a function of the stirring intensity, emulsions that after curing of the calcium phosphate paste result in a porous cement structure. Apparently, the thus obtained porous shaped bodies and granules have only minimal strengths so that a subsequent thermal treatment is required for their fortification. These compositions and the described methods for manufacture are unsuitable as cement-based preparations because, in addition to minimal mechanical strengths, they are even more difficult with respect to manufacture than the powder/liquid mixtures themselves.

WO 01/76649 A1 discloses admixture of hydrophobic liquid, in particular oil or fat, to powdery components of mineral bone cements with the goal to improve the rheologic properties of the bone cement and to facilitate the admixture of pharmacological active ingredients. In particular, the hydrophobic liquid is supposed to improve the release of pharmaceutical active ingredients (for example, vitamin E) in the body. As a result of the admixture of maximally 10% (and preferred 2-6%) of the hydrophobic liquid according to WO 01/76649 A1 a powder is obtained that before injection must be carefully and efficiently mixed.

SUMMARY OF THE INVENTION

It is an object of the invention to provide implant materials in the form of easily processable pastes, suspensions, or dispersions that under normal conditions have an extended shelf life and are usable in multiple ways, in particular also as bone cements, bone replacement materials, bone adhesives, tooth filling materials and implantable active ingredient carriers.

According to the invention the object is solved by implant materials on the basis of a hydraulic cement of at least one component in the form of a paste, suspension, or dispersions that contains at least one powdery and reactive solid containing calcium and/or magnesium compounds and that upon admixture with an aqueous liquid or after introduction into an aqueous liquid cures to a solid body. According to the invention the at least one component contains a solid and a carrier liquid that is substantially free of water and, in the chemical sense, is not miscible with water. According to the invention, the consistency of the paste, suspension, or dispersion under normal conditions does not surpass that of a kneadable compound.

Powdery and reactive solids that contain calcium and/or magnesium compounds are solids that upon mixing with an aqueous liquid or after introduction into an aqueous liquid may cure by a hydraulic cement reaction to a solid body.

The implant materials according to the invention in the form of one or several pastes, suspensions or dispersions containing mineral and/or organic and/or organo-mineral solids in a first liquid are formulated such that the pastes, suspensions, or dispersions over extended periods of time at normal conditions (normal conditions are defined as 25° C. and 101.3 kPa) have an extended shelf life and that upon combination with an aqueous second liquid or after introduction into an aqueous second liquid react by a cement-like curing reaction and cure to a solid body. In this connection, the first liquid, the carrier liquid of the mineral paste, suspension, or dispersion, is substantially free of water and is not miscible with water, in the chemical sense, or is not at all, or only minimally, soluble in water.

The miscibility with water in the chemical sense means a homogenous distribution of the carrier liquid in water at the molecular level, the molecules are thus present as individual molecules in the mixture with water. This applies, for example, to glycerine, low-molecular mono-valent and divalent alcohols, acetone, liquid polyethylene glycols etc. This is in contrast to liquids that are not miscible in the chemical sense with water and/or are soluble only minimally in water. Examples are the typical oils (even when liquids that are referred to colloquially as oils do not represent a uniform class of substances). As a limit of solubility in the context of the invention a maximal solubility of the carrier liquid in water of 25% is set, because this value differentiates soluble and insoluble liquids well. In practice, the solubility of the claimed liquids is significantly lower. The chemical miscibility is to be unequivocally differentiated from the physical miscibility because in the case of physical miscibility no molecular distribution of the liquids exists but the mixed liquids are present as aggregates, for example, as droplets of one liquid in a continuous phase of the other liquid. Typical examples are emulsions of oils in water and vice versa.

The miscibility of liquids is greatly dependent on the environmental conditions, in particular the temperature. In the context of the invention, as environmental conditions the conditions that are relevant for using the products according to the invention are decisive; these are conventionally the values referred to as normal conditions of 25° C. and 101.3 kPa.

According to the invention, the paste, suspension or dispersion under normal conditions does not surpass the consistency of a kneadable compound. Characteristic in any case is that the obtained paste, suspension or dispersion under normal conditions has a liquid to pasty consistency, depending on which carrier liquid is used as a dispersion agent and in which composition, particle size, particle shape, and concentration the dispersed solids are present and to what extent the consistency has been adjusted in a targeted fashion by further additives.

The range of the at least one component thus ranges from the consistency of relatively thin fluid dispersion paints up to the consistency of highly structure-viscous pastes, modeling materials and putty. The concentration of the dispersed solids is only one possibility to affect the consistency as evidenced by the fact that, for example, dispersion paints may have very high solids contents and despite of this have a comparatively low viscosity. A similar situation exists for the inventive dispersions of calcium phosphate cements in thin-fluid oils (for example, Miglyol 812) and the addition of surface-active agents that even for a solids contents of >75% under intensive grinding can be adjusted to the consistency of syrup. Without being limiting with respect to the embodiments of the invention, the consistency of the dispersions is primarily and preferably adjusted to the consistency of syrup or toothpaste when the use as a 2-component system and in a 2-chamber syringe is provided. A comparable consistency is preferably selected when the dispersion is employed as a single component system that is to be dispensed by means of a syringe. A significantly higher viscosity is preferably selected when a dispersion is to be provided as a single component system that is to be employed in open form. In the medical field, this can be, for example, the replacement of bone wax or the use as a bone filler in case of open implantation. Here, a high viscosity optionally with the characteristic of a strong structural viscosity is particularly preferred. Illustrative materials with respect to consistency are modeling materials, modeling clay, putties.

The gist of the present invention is the formulation of reactive mineral or organo-mineral cement components in carrier liquids that are free of water and, in the chemical sense, are not miscible with water. According to the invention the carrier liquids are not soluble or only minimally soluble (<25%) in water or water is only minimally soluble (<25%) in the carrier liquids. The (organo-)mineral powders are preferably suspended in their final mixture in these non-aqueous liquids to from a paste and in this form they are stable when stored inasmuch as the powders are finely dispersed and a suitable carrier liquid has been selected. Optionally, depending on the cement, special manufacturing steps and measures—in particular, intensive grinding, addition of surface-active agents, addition of polymers, etc.—is expedient in order to permanently ensure the stability of the dispersion.

The reactive and hydraulically curing solids that are dispersed in the liquid that is free of water and not miscible with water react as soon as the obtained pastes, suspensions or dispersions are mixed with a suitable aqueous solution or introduced into an aqueous liquid. This fact is particularly surprising because the solids that are dispersed in the liquid that is free of water and not miscible with water must first pass into the aqueous phase before they can react with one another. The composition of the aqueous solution as a medium and/or reaction partner for the curing reaction is based in the case of 2-component systems on the composition that is also used in case of conventional admixture of cements. In principle, the composition of the aqueous solution can be matched substantially freely to the intended application purpose in that, for example, the concentration of the dissolved substances is adjusted such that the preferred curing rate is obtained. It is in fact important that all components reactive with water (or with or in the water with one another) of the employed components of the hydraulic cement are dispersed in the liquid that is free of water or is not miscible with water. This has the results that accordingly all other components of the cement may also or preferably be contained in the aqueous solution. The aqueous solution accordingly may assume the consistency of a second paste in the 2-component version.

Usually, known mineral or organo-mineral reactive systems as well as implant materials on the basis of hydraulic cements require water as a medium and/or reaction partner for the curing reaction. In many cases, the typical liquid in case of powder/liquid systems in addition to water contain dissolved or suspended organic or inorganic substances (or they dissolve upon contact with water very quickly from the powder component so that they are practically available immediately after admixture) with which the kinetics of the curing reaction, the crystal structure of the cured product, the viscosity of the liquid or the cement paste, the wetting and mixing behavior etc. are affected. According to the invention, either the entire powder component or at least all of its components that may react with the aqueous solution or that may react with one another in the aqueous solution are dispersed to a paste in a non-aqueous carrier liquid that is not miscible with water in the chemical sense in which paste these powder components have an extended shelf life and in particular >6 months and preferably >2 years under normal conditions. Reactive organo-mineral cement components basically can be formulated in water-containing solutions only such that they remain substantially non-reactive in that by selection of suitable stabilizers or extreme pH values they are impaired in their reactivity. Such measures however are in contradiction to the concept of the present invention in particular with respect to the use as medical implant materials for which neither stabilizers that may impair mineralization of the bone nor extreme pH values in the acidic or alkaline range are acceptable. According to the invention, exclusively those carrier liquids are therefore considered for producing organo-mineral pastes that are practically free of water in order to describe primarily novel formulations that in their principal configuration are applicable universally to different kinds of implant materials as organo-mineral reactive systems.

Preferred are implant materials in which the organo-mineral solids are suspended/dispersed as fine powders because it is a goal of the development to require as little as possible of the carrier liquid for producing the pastes, suspension or dispersion in order to obtain in this way great freedom for the application-specific formulation of the implant material. In this connection, it has been found to be particularly advantageous when for the manufacture of the pastes, suspension or dispersion a mixing action with high energy introduction is employed. Preferred are in particular formulations in which the solid contents of the paste in the liquid is >2:1 and particularly preferred 3:1 (mass of the powder:mass of the carrier liquid) and wherein >10% of the solids (mass) have a particle size of <10 μm. Moreover, experiments show that particularly advantageous properties of the cement and especially high strength values of the pastes can be achieved when a broad particle size distribution is achieved in particular when >10% of the solids are comprised of particles <10 μm and when >10% of the solids are comprised of particles >50 μm.

When selecting the (organo-)mineral cements that are suitable for the implant materials according to the invention, there are practically no limitations because in the end all are based on the same principle, i.e., are mixed from organo-mineral powders and aqueous solutions or pure water. Gypsum as well as silicate-based cement powder can be dispersed in the same way in anhydrous carrier liquids as, for example, calcium phosphates. This holds true in particular for the various oils as carrier liquids. In deviation from organic, in particular polymeric, cement systems the implant materials according to the invention are characterized in that the reaction leading to curing and forming of a solid material substantially includes inorganic reaction partners and that these reaction partners consist of the group of the silicates, phosphates, sulfates, carbonates, oxides and hydroxides and/or their mixtures. As has already been mentioned above, commercially available cements sometimes contain large quantities of fillers that are participating only surficially in the reaction (i.e., in particular are incorporated into the cement matrix) but are participating only indirectly in the curing reaction. The participation may also reside; for example, in that a filler functions as a crystallization seed for the mineralization during the curing reaction and therefore in particular affects the curing kinetics but is itself not reacted. This holds true, for example, in case of calcium phosphate cements for the addition of precipitated hydroxyl apatite. In case of technical cements, inexpensive additives are added often also for economic reasons. According to claim 3, the implant materials, relative to the dispersed mineral solids, contain >30% salts of silicic acid and its condensates and/or salts of phosphoric acid or its condensates and/or salts of sulfuric acid and/or salts of carbonic acid or its mixtures or hydroxides and oxides.

As cations of the salts of the aforementioned acids primarily calcium and magnesium ions are considered. For technical applications, different quantities of other salts can be added. Particularly preferred, especially for the medical applications, are implant materials in which the dispersed solids are comprised to >75% of calcium and/or magnesium salts or their oxides and/or hydroxides.

A further specification especially for medical applications resides in the preferred use of calcium and magnesium salts of the ortho phosphoric acid. In commercial and in particular in experimental calcium phosphate cements already practically all existing calcium and magnesium salts of the phosphoric acid have been used (calcium phosphate cements comprise in this context also those that contain magnesium salts in significant quantities). Also included are those Ca and Mg salts, oxides and hydroxides that contain further ions, in particular Na, K, $NH_4$ and/or those that contain simultaneously Ca and Mg. Encompassed are also expressly the Ca and Mg salts of glycerophosphoric acid and those of other mono-substituted or disubstituted organic phosphoric acid esters. According to claim 5, implant materials are preferred in which the suspended mineral solids to >50% are comprised of calcium and/or magnesium phosphates. In addition, the solids may contain conventional fillers, for example, $CaCO_3$ and/or $SrCO_3$.

Especially preferred calcium compounds are monocalcium phosphate monohydrate (MCPM), monocalcium phosphate anhydrite (MCPA), dicalcium phosphate anhydrite (DCPA), dicalcium phosphate dihydrate (DCPD), octacalcium phosphate (OCP), α-tricalcium phosphate (α-TCP), β-tricalcium phosphate (β-TCP), amorphous calcium phosphate (ACP), hydroxyl apatite (HA), calcium-deficient hydroxyl apatite (CdHA), substituted hydroxyl apatite, non-stoichiometric hydroxyl apatite, nano hydroxyl apatite, tetracalcium phosphate (TTCP), calcium sulfate ($CaSO_4$), calcium sulfate hemihydrate ($CaSO_4 \times 0.5\ H_2O$), calcium sulfate dihydrate ($CaSO_4 \times 2\ H_2O$), calcium oxide (CaO), calcium hydroxide ($Ca(OH)_2$), calcium carbonate ($CaCO_3$), calcium glycerophosphate, calcium citrate, calcium lactate, calcium acetate, calcium tartrate, calcium chloride ($CaCl_2$), calcium silicate and/or their mixtures with one another and/or with other substances whose proportion is <5% by weight.

Especially preferred magnesium compounds are magnesium hydrogen phosphate ($MgHPO_4$) in the form of the hydrates and as anhydrous substance, trimagnesium phosphate ($Mg_3(PO_4)_2$), magnesium dihydrogen phosphate ($Mg(H_2PO_4)_2$) in the form of the hydrate and as anhydrous substance, magnesium chloride ($MgCl_2$) in the form of the hydrate and as anhydrous substance, magnesium glycerophosphate, magnesium hydroxide ($Mg(OH)_2$), magnesium hydroxide carbonate (e.g. as $4\ MgCO_3 \times Mg(OH)_2 \times 5\ H_2O$), magnesium oxide (MgO), magnesium citrate ($Mg_3(C_6H_5O_7)_2$ or $Mg(C_6H_6O_7)$), calcium magnesium carbonate ($CaMg(CO_3)_2$, dolomite) and/or their mixtures with one another (and/or with other substances whose proportion is <5% by weight).

From the plurality of calcium phosphate cements (CP cements) that are possible and described in the literature especially those are preferred that are based on the use of meta-stable calcium phosphates that under suitable environmental conditions or reaction conditions alone or with reaction partners spontaneously convert into one of the thermodynamically more stable forms—hydroxyl apatite, Ca-deficient hydroxyl apatite, substituted hydroxyl apatite or calcium hydrogen phosphate. Primarily these CP cements cure under conditions that are still beneficial to the biological system of the bone. Described are also cement systems that contain crystalline phosphoric acid or calcium oxide and therefore, at least for a brief period of time, generate extreme pH values of <4 or >10 in the environment wherein in particular the lower extremes are detrimental to bone. In principle, the administration forms of the present invention are also better suited for the latter (extreme) cement formulations than the conventional forms because the reaction space is more limited and the spacing of the reaction partners from one another may be defined better. Especially preferred are CP cements that as main components contain MCPM, MCPA, DCPA, DCPD, OCP, α-TCP, β-TCP, ACP, HA, CdHA, substituted HA, non-stoichiometric HA, nano HA, TTCP, $CaSO_4$, $CaSO_4 \times 0.5\ H_2O$, $CaSO_4 \times 2\ H_2O$, CaO, $Ca(OH)_2$ or $CaCO_3$ or their mixtures. For the medical application according to claim 8, implant materials are especially preferred in which the suspended mineral solids to >25% are comprised of the α or β modification of tricalcium phosphate (TCP), of TTCP (tetracalcium phosphate), DCPA (dicalcium phosphate anhydrite) or ACP (amorphous calcium phosphate).

In the newer literature moreover for the medical use also cements are disclosed that cure in the crystal structure of struvite or contain struvite as a determining proportion of the cured cement (EP 1296909 B1: Magnesium-ammonium-phosphate cements, the production thereof and the Use thereof) These magnesium-ammonium-phosphate cements contain typically significant proportions of calcium phosphate and represent a special embodiment of the implant materials according to the invention. For these struvite cements it is disclosed that they have excellent cohesion and relatively quickly after admixture have a steep strength increase (Schwardt et al., Kyphos FS™ Calcium Phosphate for Balloon Kyphoplasty: Verification of Compressive Strength and Instructions for Use. European Cells and Materials vol. 11, suppl. 1. 2006 (page 28)). According to claim 9, the combination magnesium-ammonium-phosphate-based implant materials with hydrophobic liquids that are immiscible with water as a paste provides a further preferred embodiment of the invention. For this purpose, the solids also contain ammonium salts that with one of the magnesium compounds cure to a magnesium-ammonium-phosphate solid substance. The ammonium salts are selected in this connection from diammonium hydrogen phosphate, ammonium dihydrogen phosphate, ammonium sulfate and ammonium acetate and water-soluble ammonium salts that contain biocompatible anions.

Technical as well as medical mineral reactive systems contain often fillers. For the medical applications especially those fillers are important that do not participate directly in the cement reaction but contribute to the cement reaction taking place under substantially physiological conditions. This applies especially to hydrogen phosphates of Ca and Mg, for the hydrates as well as the anhydrous substances. Because of their higher solubility compared to the tricalcium phosphate and the distinct buffering action in the neutral range, these hydrogen phosphates exhibit a strong buffering action with respect to possibly occurring extremes of the pH values or ion concentrations in the curing reaction. According to a further configuration according to claim 10, the implant materials contain as mineral solids to >5% calcium or magnesium hydrogen phosphate ($CaHPO_4$ oder $MgHPO_4$) as hydrate or anhydrous substance. The hydrogen phosphates of Mg or Ca play in this connection a special role because they are in the long run also reacted. In the case of struvite cements in combination with ammonium salts, magnesium hydrogen phosphate is even the reaction-determining partner. A further important filler is calcium carbonate that is also converted in the long run.

For many years, implant materials have also been in use for medical application that are comprised of calcium sulfates, i.e., gypsum. Additionally, for some years now there are also developments that, aside from calcium sulfates, also contain calcium phosphate (PCT/SE99/02475). The calcium sulfates serve in general as a binder for the calcium phosphates that in this case usually are non-reactive, i.e., they themselves do not exhibit a curing reaction. However, there are literature reports available in which cements of reactive calcium phosphate and calcium sulfates, have been produced. In both cases the formulations according to the invention are usable without limitation. According to claim 11, implant materials are claimed in which the suspended mineral solids contain >10% calcium sulfate and in particular >10% calcium sulfate hemihydrate.

With respect to the different CP cements for medical applications in particular those are of interest and preferred that, as a reaction product, result in a composition that is similar to that of bone minerals. According to claim 12, implant materials are therefore preferred in which the end product of the cement-like curing reaction with an aqueous solution or pure water results in >50% hydroxyl apatite, calcium-deficient hydroxyl apatite, substituted hydroxyl apatite and/or nano-crystalline hydroxyl apatite or their mixtures and wherein the end product has a molar calcium/phosphate ratio (C/P ratio) of >1.35. The C/P ratio of stoichiometric hydroxyl apatite (HA) is 1.67, that of calcium-deficient HA is 1.5. The selected limit of 1.35 takes into account the fact that even lower C/P ratios than 1.5 still crystallize as HA and that relatively high substitution levels may occur. According to claim 12 implant materials are therefore claimed that as a sum of their calcium and phosphate compounds have a C/P ratio of >1.35.

Examples of different calcium phosphate cements that are curing as HA or Ca-deficient HA or substituted HA or nano-HA or HA of little crystallinity are described several times in the literature since approximately 1986 (Brown W E, Chow L C: A new calcium phosphate water setting cement. In: Brown P W, editor. Cements research progress. Westerville, Ohio: American Ceramic Society; 1986. p. 352-79). In the following some literature citations in regard to especially important calcium phosphate cements:
1. Chow (s.o.)
2. US000005336264A (Constanz, Norian Corporation)
3. U.S. Pat. No. 6,117,456 (Lee, et al; ETEX Corporation)
4. U.S. Pat. No. 5,262,166 (Sung-Tsuen Liu)
5. EP 1 302 453 A1 (Hirano; Mitsubishi)
6. Bohner M, Merkle H P, van Landuyt P, Trophardy G, Lemaitre J. Effect of several additives and their admixtures on the phisico-chemical properties of a calcium phosphate cement. J Mater Sci Mater Med 2000; 11: 111-116

Driessens F C M, Boltong M G, Bermudez O, Planell J A, Effective formulations for the preparation of calcium phosphate bone cements. J Mater Sci Mater Med. 1994; 5: 164-170

Hydroxyl apatite (HA) is stable under physiological conditions and is therefore decomposed only cellularly like the bone minerals. Known as a substantially more easily dissolvable substance is calcium hydrogen phosphate dihydrate (DCPD). CP cements with DCPD as a curing product are also disclosed in the literature and are primarily favored for applications in which a relatively quick dissolution of the material is desired. Conventional starting materials for DCPD cements are β-TCP and monocalcium phosphate. The reaction product in case of use of pure starting materials has a C/P ratio of 1. Implant materials in which the end product of the cement-like curing reaction with an aqueous solution or pure water is >50% calcium hydrogen phosphate and wherein the end product has a molar calcium/phosphate ratio of 0.9-1.35 are an advantageous and especially claimed embodiment of the present invention according to claim 13. Accordingly, the implant materials in the sum of their calcium and phosphate compounds have a C/P ratio of 0.9 to 1.35.

Independent of the composition of the reactive organo-mineral substances as solids, the main aspect of the invention is the introduction of these substances into a non-aqueous carrier liquid wherein this carrier liquid is preferably an organic liquid that is immiscible in the chemical sense with water and in water is practically insoluble and in which water is also essentially practically insoluble. A value of 25% (relative to the volume) is viewed as a limit for the mutual solubility. In general and preferred this limit is substantially lower, i.e. approximately <10% and especially preferred <5%. Liquids to which this applies are sufficiently known to the layperson as well as the person skilled in the art. For medical applications, in particular pharmaceutical, cosmetic and food-technological liquid excipients are considered that fulfill the above specifications.

While the liquid is not soluble or only minimally soluble in water, it still contains according to claim 15 preferably solid or liquid dispersed substances that are easily soluble in water or at least are greatly swellable or in the chemical sense are miscible with water. These can be reactive substances of the cement or those that affect the reactivity of the cement without themselves participating in the reaction to a significant degree. Moreover, excipients that enhance the dispersion of the cement in the organic liquid, improve the miscibility of the paste with an aqueous liquid, act as active ingredients or serve to generate in the final cement a pore system. The latter applies in particular to lightly crosslinked polyelectrolytes as they are known as superabsorbers and, for example, are comprised of lightly crosslinked polyacrylic acid or carboxymethyl starch. In particular, these substances have the function to dissolve very quickly in water and to affect the viscosity of the aqueous phase such that a macroscopically homogenous physical mixture of both phases can be formed.

For triggering the cement-like curing reaction of the implant materials the dispersed solids in the organic liquid must be brought into intimate contact with the/an aqueous solution or pure water so that these solids at least partially may dissolve in water and recrystallize or precipitate in the aqueous phase. For this purpose, an intimate admixture of the paste with an aqueous solution in the sense of a physical mixture (i.e., in particular the formation of an emulsion and/or dispersion) must take place wherein a surface area as large as possible is formed as a phase boundary through which the water and the solids may contact one another and through which the dissolution of the water-soluble components of the paste is enabled. It is known to the person skilled in the art that the various organic liquids that are immiscible with water in the chemical sense are suitable in various ways to produce physical mixtures with water. The formation and stability of such physical mixtures depends in addition to the type of liquids significantly on the introduced energy during mixing of the participating partners. Since during mixing of the pastes according to the invention with aqueous solutions in general no structurally complex devices for introducing high energy quantities are available, the selection of organic liquids is of great importance. The required energy for mixing the liquids can be greatly reduced by surface-active agents and in special cases so much that emulsions—in particular microemulsions—are formed spontaneously between the otherwise immiscible liquids. This aspect is of decisive importance for the invention as has been demonstrated by experiments, not disclosed in detail here, with liquids that are not easily miscible (pastes and aqueous solutions) in which a manual mixing action practically is not possible and no curing reaction or formation of a solid material was observed.

An important aspect of the invention are therefore implant materials in which the organic liquid that is serving as a carrier medium for the paste is miscible with water and/or aqueous solutions in the physical sense and/or wherein the organic liquid contains substances that assist in the formation of a physical mixture with water or aqueous solutions (formation of an emulsion) and can stabilize it. Such substances may be surface-active agents or highly dispersed solids; see in this respect monograph "Die Tenside", Kosswig/Stache, Carl Hanser Verlag München Wien, 1993, ISBN 3-446-16201-1. In regard to the topic of emulsions reference is being had to the publication "Makro- und Mikroemulsionen" by H.-D. Dörfier: Grenzflächen und kolloid-disperse Systeme. Springer, Berlin, 2002, chapter 13.

In a special embodiment of the invention according to claim 17, the spontaneous formation of microemulsions between the paste and the aqueous solution is the goal. In contrast to macroemulsions that require for formation usually energy introduction and are thermodynamically instable, the microemulsions also spontaneously form under environmental conditions and are thermodynamically stable. They contain in addition to an aqueous phase and an organic (oil) phase at least one surface-active agent and a low-molecular organic liquid that is usually referred to as a surface-active co-agent or solubilizer that is, for example, a short-chain to medium-chain alcohol; however, many other organic liquids may also be considered for this purpose. Like the surface-active agents or emulsifying agents, the surface-active co-agents or solubilizers may also be present in the paste or the aqueous solution. In general, this selection depends primarily on the better solubility of the additive in the respective phase. According to the invention claimed are therefore in this special embodiment implant materials in which the organic liquid is comprised of at least 2 substances that are liquid under normal conditions and wherein each of the substances is contained to at least 0.1% in the first liquid. In this embodiment, the specification of minimal water solubility of the organic liquid only applies to one of the two substances that together form the organic liquid.

As already explained above, many organic liquids are suitable as carrier liquids for the organo-mineral phase according to the invention. Principally unsuitable are those liquids that have a very low boiling point and may have explosive potential, are subject to limitations because of toxicological reasons, make difficult the incorporation of powdery solids because of their high viscosity, solidify already near normal temperature or are incompatible with one or several of the organo-mineral solids or may undergo undesirable reactions. Unsuitable are also organic liquids that as such are not stable when stored or, for achieving an extended shelf life, require complex measures. As examples the basically very well suited oils (triglycerides) shall be mentioned wherein in this group those representatives are to be considered unsuitable that without complex measures have the tendency to turn rancid. For the preferred use of the implant materials according to the invention as implantable medical products or pharmaceutical product, reference is being had to "Fiedler—Lexikon der Hilfsstoffe" (edition 01/2002). Preferred are mixtures of two or more organic liquids by means of which special properties of the paste can be obtained. In this sense, according to claim 18 primarily implant materials are claimed in which the organic liquid to >50% is comprised of aliphatic hydrocarbons, esters, ethers, substantially water-insoluble organic acids or substantially water-insoluble mono-valent multi-valent alcohols with a molecular weight of <2,500 or their mixtures.

Especially preferred with respect to a medical or medical-engineering application are substantially water-insoluble and non-toxic organic liquids that can be easily metabolized in the body or excreted. Moreover, such organic liquids are preferred that under normal conditions have a low viscosity in order to facilitate in this way the incorporation of (organo-)mineral powders. Especially preferred are organic liquids listed in the following, their homologues, their mixtures with one another and with their homologues: glycerine triacetate, glycerine tributyrate, glycerine trioleate, glycerine dioleate, glycerine monooleate, caprylocaprate, decyloleate, isopropyl myristate, isopropyl palmitate, oleic acid, oleyl alcohol, oleyl oleate, short-chain triglycerides, medium-chain triglycerides (e.g. Myritol® 318 PH, Miglyol 810, Miglyol® 812, Miglyol® 829), short-chain and medium-chain fatty acid esters of propylene glycol (e.g. Miglyol® 840), ethylbenzoyl acetate, ethylbutyrate, ethylbutyryl acetate, ethyl oleate, ethyl caproate, ethyl caprylate, ethyl caprate, ethyl laurate, ethyl laevulinate, ethyl myristate, ethyl palmitate, ethyl linoleate, ethyl stearate, ricinoleic acid, linolic acid, linolenic acid, arachidic acid, oleic acid, ethylarachidate, α-tocopherol, β-tocopherol, γ-tocopherol, δ-tocopherol, benzyl alcohol, benzyl benzoate, diethylbutyl malonate, diethylenglycol dibutylether, diethylethylmalonate, diethylphenylmalonate, diethylphthalate, diethylsebaceate, diethylsuberate, diethylsuccinate, dibutylmaleinate, dibutylphthalate, lecithin, paraffin oil, petrolatum, liquid paraffins, ester of sebacic acid, especially sebacic acid dibutylester, sebacic acid diethylester, sebacic acid diisopropylester, sebacic acid dioctylester. Among the aforementioned hydrophobic organic liquids especially preferred are the thin fluid short-chain and medium-chain triglycerides and medium-chain fatty acid esters of propylene glycol, alone and in combination with one another and with other substances. For the medical application, particularly preferred ones of the aforementioned substances and their derivatives and homologues are those that fulfill CFR 21 (Code of Federal Regulations) and are classified as "GRAS" (generally recognized as safe).

For use as implant materials and active ingredient carriers particularly neutral oils with relatively low viscosity are of interest as the organic liquids. They are typically esters of glycerine or propylene glycol with relatively short-chain fatty acids. From this group the mono-, di- as well as triglycerides are of interest. While the triglycerides practically are immiscible with water, mono- and diglycerides, depending on the composition, can easily form with water emulsions or micellar solutions. These aggregates that may give the impression of being molecular solutions do not contradict the limitation of the independent claim according to which the carrier liquid in the chemical sense is not miscible with water because here also mixtures in the physical sense with the formation of phase boundaries are present. In addition to fatty acid esters of the glycerine also fatty acid esters of other mono-valent or multi-valent alcohols are to be considered, in particular those of ethylene glycol and of propylene glycol (propanediol) and moreover especially preferred the fatty acid esters of liquid oligomers and/or co-oligomers of ethylene glycol and propylene glycol. Further preferred esters of multi-valent alcohols are those of sugars and sugar alcohols, as in particular that of sorbite, sorbitan, and xylitol. The reason for preferring such esters is the simple biological decomposition or enzymatic cleavability with subsequent excretion or metabolic decomposition of the cleaved products. A further reason is the simple synthetic accessibility of these substances so that a great variability of liquids is available or can be made available and thus can be matched to the requirements, respectively. Claimed are therefore in general implant materials in which the organic liquid primarily, i.e., >50%, is comprised of esters of mono- and/or multi-valent alcohols with fatty acids.

A special form of the pastes according to the invention contains, as a carrier liquid, liquid oligomers of hydroxy acids that are also used for the synthesis of resorbable polymers. Most widely used are polymers of lactic acid, glycolic acid, hydroxy butanoic acid, of caprolactone and their copolymers. Compounds of these hydroxy acids with low degree of polymerization are viscous liquids at normal conditions. The oligoesters of the aforementioned hydroxy acids with mono-valent or multi-valent alcohols are considered especially suitable carrier liquids in this group. These compounds are synthetically easily accessible and can be tailored with respect to their properties in a wide range based on the ratio of alcohol to hydroxy acids and the ratio of the mixture of the hydroxy acids with one another. Examples are ethylene glycol oligolactide or glycerine oligolactide that, at a molar ratio of alcohol to lactic acid of >0.1, constitute flowable viscous liquids that are stable when stored under exclusion of water and are immiscible with water. Advantageous is in connection with these carrier liquids the easy biological decomposition and the excellent compatibility with bone that, for example, has led to utilization of these oligomers for use in resorbable bone waxes (DE 19858891; 19981219). Experiments, not explained herein in detail, have shown that large quantities of mineral solids (as described above) can be incorporated into these viscous liquids without problem. According to the invention implant materials are therefore claimed in which the organic liquid to >50% is comprised of esters or oligoesters of mono-valent or multi-valent alcohols with hydroxy acids, in particular of lactic acid, glycolic acid, hydroxy butanoic acid, caprolactone, their mixtures, co-oligomers and or stereoisomers.

For implant materials moreover the liquid oligomeric and polymeric derivatives of ethylene glycol (EO) and propylene glycol (PO) are especially suitable because also the representatives of these substance group are biologically particularly compatible and have versatile uses as excipients in pharmaceuticals, medical products and cosmetics (Pluronics and Tetronics). Belonging to this group are also all compounds that, in addition to EO units and/or PO units, contain further building blocks to less than 50% (mass). Therefore, this group comprises in addition to PEG (polyethylene glycol) and PPG (polypropylene glycol) especially preferred copolymers/co-oligomers of these building blocks that may have a random sequence of the units but may also exist as block copolymers/co-oligomers. Also especially preferred are (co)polymers/(co-)oligomers that contain further units of the following compounds: alcohols, fatty acids, sugars, sugar alcohols, amines. In addition to PEG and PPG, typical representatives of this group are their copolymers, alcohol ethoxylates, fatty acid ethoxylates, fatty amine ethoxylates, sugar ethoxylates, ethoxylates of fatty acid esters of multi-valent alcohols and sugars, as in particular the ethoxylates of the fatty acid esters of sorbite/sorbitan, and in this connection in particular the representatives of the type of Tween and Span products (Brij; Triton). In general, in this connection implant materials are claimed in which the organic liquid to >0.1% is comprised of oligomers or polymers and/or co-oligomers or copolymers of ethylene glycol and/or propylene glycol with one another and other building blocks wherein the ethylene glycol and propylene glycol units together make up more than 50% (mass) of the corresponding compound and wherein the compounds at normal conditions are liquid. The above mentioned substances and substance groups are at least partially water-soluble. In these cases they are preferably claimed as components of the carrier liquid together with the water-insoluble substances. The water-insoluble representative may also be used alone or in combination with further substances as a main component of the carrier liquid.

The application possibilities of the implant materials according to the invention are very versatile and range in case of medical applications from the use as implantable active ingredient carrier that is exposed only to minimal mechanical load to bone cement for the fixation of implants, augmentation of mechanically highly loaded bone and reconstruction of skeletal structures that in many cases are exposed to high loads. The great advantage of the implant materials according to the invention is the possibility of adaptation of the properties to the respective fields of use. An important parameter in this connection is the quantity of organo-mineral solids which are dispersed in the paste. According to the invention it must be so high that a curing reaction between the particles of the solid dispersion can be ensured when the latter is mixed with the aqueous solution. The critical concentration of (reactive) solid particles depends greatly on various factors. In addition to the type of reactive solids, primarily the particle size and particle shape play a decisive role. In a select embodiment of the invention according to claim 22, the implant materials contain the dispersed mineral solids to 25% up to 75% (weight %) in the paste that is comprised of organic liquid and solids. In this embodiment the solids particles at least partially are present in a comparatively highly dispersed form as, for example, may be the case for nano-dimensioned calcium phosphates, calcium carbonates, calcium hydroxides, calcium oxides, calcium sulfates, calcium citrates, magnesium oxides, magnesium hydroxide carbonates, silicates of various cations and reactive glasses (as they are used for glass-ionomer cements) that are produced by sol/gel methods. Field of application are primarily active ingredient carriers and bone filling substances with a very high biological activity.

In the following exemplary compositions for the use as an active ingredient carrier or bone filling material with minimal mechanical load (weight percent) are listed:

| reactive mineral powder (mixture) | carrier liquid | surface-active agents (see below) | mineral fillers | active ingredients |
|---|---|---|---|---|
| 25-75 | 20-50 | 0.1-15 | 0-50 | 0-25 |
| *) 50-70 | 20-35 | 0.5-10 | 0-20 | 0-10 |

*) Implant materials with a reactive mineral powder mixture with a proportion of 50-70% by weight are preferred in this context.

The listed compositions are also suitable for 2-component systems wherein the compositions listed in the table apply to the anhydrous component.

In a further embodiment the focus is on a specially high solids content of the paste according to the invention with the goal to obtain cements with a high strength. This concerns practically all technical applications and in the medical field in particular the use as bone cements and bone filling materials for high loads. The subject matter of this embodiment are implant materials in which the dispersed organo-mineral solids are contained to >75% (weight percent) in the paste comprised of the organic liquid and solids. Examples of this embodiment are disclosed in the examples. Especially high contents of solids can be obtained when the reactive solids are combined as powder with the carrier liquid and subsequently are mixed with high energy introduction and further comminuted as disclosed in the example. In this way, degrees of filling of >80% can be achieved with solids mixtures that consist primarily of calcium phosphates. A further increase of the solids contents can be achieved by admixture of further—typically relatively coarse solids—into the premixed paste so that when mixing a paste of oil and calcium phosphates that already has a solids content of 70% by admixture of sintered substantially dense particles of β-TCP in a ratio of 1:1 a paste with a solids contents of >85% may be obtained. This procedure can also be applied to other material systems and represents an especially preferred embodiment of the invention. Claimed are therefore implant materials in which the dispersed organo-mineral solids are contained by >70% (weight percent) in the paste comprised of organic liquid and solids.

In the following in an exemplary fashion a composition for use as a bone filler, as an active ingredient carrier or bone cement with high mechanical load (weight percent) is listed:

| reactive mineral powder (mixture) | carrier liquid | surface-active agents (see below) | mineral or organic fillers | active ingredients |
|---|---|---|---|---|
| 75-85 | 10-25 | 0-5 | 0.5 | 0-5 |

The listed compositions are also suitable for 2-component systems wherein the compositions in the table apply to the anhydrous component.

The use of substances that upon mixing of powders with liquids and of liquids with one another or with pastes have an enhancing effect are of prominent importance in the present invention. Some of the suitable surface-active agents or substances, that in addition to other effects also may act as surface-active agents, are present in liquid form and, as mentioned above, can also be used as a part of the carrier liquid or as the carrier liquid itself. However, it is expressly noted here that also surface-active agents that are present at normal conditions as solids may advantageously be used in the implant materials according to the invention as also illustrated in example 2 (Amphisol A and SDS are also solids at room temperature). Some experiments have shown that the addition of surface-active agents favors the admixture of the solids into the carrier liquid greatly and in particular may affect the admixture of the obtained paste with an aqueous solution decisively. A comprehensive listing of suitable surface-active agents will not be provided here because such a list in no way could be complete and, in view of the various compositions of the products according to the invention and the numerous potential fields of application, there is practically no surface-active agent that could be excluded for objective reasons. As background information and as an overview reference is being had again to the monograph "Die Tenside". Claimed are therefore all implant materials in which the paste, in addition to suspended/dispersed organo-mineral solids and organic liquid, contains one or more surface-active agents. In the following, some preferred groups of surface-active agents will be mentioned especially, in particular those that are considered for medical-engineering/pharmaceutical application.

anionic surface-active agents
    fatty acids and their salts (Na, K, $NH_4$, Ca, Mg, Zn, Fe)
        e.g. sodium oleate, sodium palmitate
    esters of fatty acids and their salts
        e.g. sodium dilaureth-7-citrate, stearoyl disodium tartrate
    carboxylic acid ethers
        e.g. fatty alcohol polyglycol ether carboxylic acid (and salts)
    alkyl sulfate/alkylether sulfates (and their salts)
        e.g. sodium alkyl sulfate (esp. sodium lauryl sulfate)
    alkyl sulfonate
        e.g. sodium lauryl sulfonate
    sulfosuccinate
        e.g. sodium dialkyl sulfosuccinate
    phosphoric acid ester (alkyl and alkylether phosphates) and their salts
    mono- and dialkyl phosphoric acid esters
    acyl amino acids and their salts
    acyl glutamates, acyl peptides, acyl sarcosides
cationic surface-active agents
    alkyl amine salts
    alkyl imidazolines
    tetraalkyl(aryl) ammonium salts
    heterocyclic ammonium salts
        e.g. alkyl ethyl morpholine ethosulfate
    ethoxylated amines
        e.g. polyethylene glycol-6-lauryl amine
amphoteric surface-active agents
    acyl ethyldiamine and derivatives
    N-alkyl amino acids and/or imino-dicarboxylic acids
    betaines
        e.g. alkyl amido propyl betaine
    lecithins
non-ionic surface-active agents
    fatty alcohols
        e.g. decyl alcohol, dodecyl alcohol (especially preferred als surface-active co-agents)
    ethoxylated fatty alcohols
        $CH_3(CH_2)_x$—O—$(CH_2CH_2O)_y$-H with x=8-18 and y=appr. 2-appr. 300
    ethylene oxide/propylene oxide-block copolymers
    alkyl phenol ethoxylates alkyl polyglucosides
ethoxylated fats and oils
alkanol amides
ethoxylated alkanol amides
polyethylene glycol fatty acid esters
glycol- and glycolesters
   ethylene glycol fatty acid esters
   propylene glycol fatty acid esters
   glycerine fatty acid ester (mono- and diesters)
sorbitan ester (mono- and triesters)
sugar esters
ester/ether surface-active agents
   ethoxylated glycol- and glycerine esters
   ethoxylated sorbitan esters
      ethoxylated sorbitan ester of the fatty acids lauric, myristic, palmitic, stearic and oleic acids (e.g. Tween types)
polyglycerine monoesters
amine oxide
alkoxylated polysiloxanes (silicone-based surface-active agents)
fluorine-based surface-active agents The two groups listed last have primarily technical application potential in combination with the implant materials according to the invention.

In the following therefore only a few select surface-active agents shall be mentioned whose use in the implant materials according to the invention is preferred (however, other surface-active agents, derivatives or homologues of the aforementioned surface-active agents are not meant to be excluded in any way): sodium lauryl sulfate, glycerine monooleate, polysorbate 20, 21, 40, 60, 61, 65, 80, 81, 85, 120, sorbitan diisostearate, sorbitan dioleate, sorbitan monoisostearate, sorbitan monolaurate, sorbitan monooleate, sorbitan monopalmitate, sorbitan monostearate, sorbitan trioleate, sorbitan trilaurate, sorbitan tricaprylate/caprate, isopropyl myristate, lecithin, lysolecithins, oleic acid, oleic acid, polyethylene glycol monocetyl ether, polyethylene glycol monostearyl ether, polyethylene glycol monolauryl ether, polyethylene glycol monooleyl ether, polyethoxylated ricinus oil, polyoxyl-40-stearate, polyoxyl-50-stearate, ascorbyl palmitate, cetyl phosphate ((Amphisol®) and its salts), PEG cetyl stearyl ether (ceteareth-6 (-11, -25), cetyl/stearyl alcohol (cremophor A® types).

Especially preferred for the medical-engineering and pharmaceutical application of the present invention are surface-active agents that are already used in pharmaceutical preparations. Especially to be mentioned are products that are offered under the name Tween 20, Tween 80, Pluronic F68, and Cremophor as well as lecithin. Moreover, especially preferred are fatty acids and their salts and the medium-chain fatty alcohols.

Aside from surface-active agents, also finest dispersed solids may enhance the formation and stability of physical mixtures between solids and liquids and liquids with one another (see the publication "Makro- und Mikroemulsionen" by H.-D. Dörfler: Grenzflächen und kolloid-disperse Systeme. Springer, Berlin, 2002, chapter 13). Claimed are therefore in particular also all embodiments of the implant materials according to the invention in which the paste, in addition to suspended/dispersed organo-mineral solids that are participating in the cement-like curing reaction, organic liquid and optionally further excipients and active ingredients, may contain iron oxide, clay minerals, silicon dioxides, barium sulfate, or glycerine stearate as highly dispersed solids that assist in the formation and stability of physical mixtures (emulsions). The above list is not meant to be complete and therefore also shall encompass other substances that act in the same way.

Among the furthermore meaningful and/or required excipients for optimal preparation of the products according to the invention. polymers are of special importance. By means of polymers in particular the viscosity of the paste and its shelf life can be affected. Moreover, they have an effect on the cohesion of the paste which may be of great importance in particular in the embodiment as a single-component system. In medical applications they may increase the biological activity or the resorbing action. As polymers in particular the biopolymers collagen and its derivatives (inter alia also gelatin), starch and its derivatives (in particular hydroxyethyl starch and carboxy methyl starch), cellulose derivatives, chitin/chitosan derivatives and the synthetic polymers polyvinyl alcohol, polyvinyl pyrrolidone, poly acrylic acid, polymethacrylic acid, other polyacrylic derivatives (for example, polyacrylic acid derivatives of the company Degussa known under the trademark Euragit), high-molecular PEG and PPG derivatives (in particular also high molecular Pluronics and Tetronics and homologue polyethers). The above list is not meant to be complete and therefore is meant to encompass also other substances that act in a similar way. Claimed are generally implant materials in which the paste in addition to suspended/dispersed organo-mineral solids and organic liquid and one or several surface-active agents and/or highly dispersed solids contains dissolved or suspended polymers with a molecular weight of >2,500.

Special mention in this connection is to be made of polymers, highly dispersed solids and surface-active agents that, even through they are included in the paste, develop their function however during and after admixture with an aqueous solution primarily by affecting the properties of the aqueous solution. This relates in particular to the formation of the emulsion of organic liquid and aqueous solution by means of affecting viscosity and surface tension.

The implant materials according to the invention are downright predestined for the use as active ingredient carriers in the bone and dental area, in particular for active ingredients that are acting locally. The possibility to be able to supply these active ingredients either in the organic-based paste or in the aqueous solution makes these materials practicable for all relevant active ingredient classes as a suitable carrier material. Moreover, the porosity of the cured solid material can be adjusted in wide ranges in order to match thus also the release kinetics with respect to the requirements. The use of suitable excipients as in particular the aforementioned highly dispersed solids, surface-active agents, and polymers, moreover allows for further fine adjustment of the active ingredient release. As suitable active ingredients all substances relevant for local treatment of bone diseases are to be considered in particular those with an antimicrobial action (such as e.g. antibiotics, antiseptics, antimicrobial peptides), an anti-tumor action (e.g. cytostatic agents, antibodies, hormones), anti-resorption action (e.g. bisphosphonates, corticosteroids, fluorine, proton pump inhibitors), anti-inflammatory action, bone growth-stimulation action (growth factors, vitamins, hormones, morphogens) etc. In this connection the above list is also not meant to be complete and therefore shall encompass also other substances that locally may act in bone and the surrounding tissues and may enhance the function of the implant material in the desired way. As a whole, all implant materials are claimed in which the paste, in addition to the dispersed organo-mineral solids and the organic liquid, contains one or several dissolved or suspended pharmacological active ingredients.

According to claim 29, the implant materials according to the invention contain in addition to the paste/suspension or dispersion as a further component and aqueous solution or pure water. In this embodiment, the implant material according to the invention is designed such that the paste produced according to one of the above specifications from organic liquid and dispersed solids is mixed with a defined aqueous solution or optionally pure water (a special form of the defined solution) and this mixture subsequently cures to a solid material.

This embodiment has in comparison to the second embodiment mentioned farther below the advantage that the aqueous solution may be adjusted such that the curing action as well as further properties of the final product can be affected in a targeted fashion. For this purpose, the aqueous solution may have substances added to it that participate themselves in the curing reaction and affect their kinetics. Moreover, the aqueous solution may have special substances added to it that affect mixing of the aqueous solution with the paste in a desired way. Basically, these include all non-reactive components of mineral cements, in particular fillers and active ingredients that may also be formulated within the aqueous solution. They may be present therein in dissolved as well as dispersed or suspended form. The aqueous solution can therefore also assume the character of a paste that contains a significant solids content. Since the homogenous mixing of anhydrous paste with the aqueous solution in a 2-component system succeeds best when viscosities and consistencies of the two components are as close as possible, the formulation of the aqueous solution with suspended fillers, highly dispersed solids and/or dissolved or swelled polymers is a preferred embodiment of the invention. Examples of suitable fillers are $CaCO_3$, finely dispersed calcium phosphates (in particular nano-crystalline hydroxyl apatite), finely dispersed magnesium phosphates or carbonates, highly dispersed silicic acids or their salts and polymers dissolved in colloidal form.

To be mentioned especially are additives to the aqueous solution by means of which its viscosity can be affected, i.e., in particular additives of polymers, highly dispersed solids, and surface-active agents of which some (as in particular the highly ethoxylated sorbitan esters and Pluronics (PEG-PPG block copolymers)) form viscous gels, important for products according to the invention, with aqueous solutions in certain concentrations.

According to the embodiment of claim 31 non-reactive components of the mineral cement solids are partially or completely contained in the aqueous solution.

Special mention shall be made of substances as additive to the aqueous solution that themselves do not participate in the curing reaction of the mineral solids but, for example, may have an effect on their crystal structure and therefore may decisively modify the properties of the end products to be formed. This may be polymer substances such as hyaluronic acid, chondroitin sulfate, or polyacrylates, low-molecular organic substances such as citric acid, tartaric acid, amino acids, sugars and their derivatives and their respective salts, or inorganic substances wherein the latter in general are incorporated into the crystal structure at least partially.

Relevant active ingredients may also be dissolved in the aqueous solution or suspended therein inasmuch as in this form they are of satisfactory stability. The chemical stability and the release kinetics determine in this connection substantially whether an active ingredient is preferably supplied in the oil phase or water phase.

In principle, the implant materials according to the invention that are comprised of two or several components, can be combined in various ways with one another and mixed in order to trigger in this way a curing reaction and to achieve the formation of a solid material. Especially preferred in this connection is however that the respective component in the form of a paste or a (viscous) liquid is supplied in a container and the components of the implant material before or during use are combined with one another and combined with a mixing device such that, by means of this mixing device, they can be homogeneously mixed on a macroscopic level. In the simplest situation, for this purpose 2 pastes of which one is the oily phase and the second is the aqueous phase are filled into separate cartridges, respectively. Immediately before application the cartridges are then connected to one another by an opening at one of their ends by a T-piece and then connected to a static mixer. The two cartridges are then dispensed by means of a device that ensures uniform dispensing of both cartridges. When doing so, the two pastes are forced into the static mixer and upon passing through are macroscopically homogeneously mixed with one another. Such devices are known in principle and are used, for example, for mixing fibrinogen and thrombin when used as an autologous fibrin adhesive. In the context of this invention they are described for the first time for mixing the implant material according to the invention.

Exemplary compositions of 2-component systems for use as a bone filler or bone cement (values in weight percent relative to the total contents of the respective component):

Anhydrous Paste (Paste 1)

| reactive mineral powder (mixture) | carrier liquid (oil) | surface-active agents | mineral or organic fillers | active ingredients |
| --- | --- | --- | --- | --- |
| *) 25-75 | 10-49 | 0.1-15 | 0-50 | 0-25 |
| **) 70-89 | 10-29 | 0.1-15 | 0-19 | 0-19 |

*) preferred use as active ingredient carrier and minimally loaded filler
**) preferred use as bone filler, active ingredient carrier or bone cement with high loadability Aqueous Solution (Paste 2)

| water | water-soluble polymer | surface-active agents | mineral or organic fillers/ curing accelerator | active ingredients |
| --- | --- | --- | --- | --- |
| 25-100 | 0-30 | 0-15 | 0-70 | 0-25 |

Both components can be mixed with one another in wide ranges. Preferred are mixing ratios in the range between 10:1 and 1:1 (paste 1: paste 2); curing accelerators are substances dissolved or suspended in the aqueous solution (e.g. phosphate salts or organic acids or their salts) that have an effect on the cuing reaction of the mineral cement.

In an especially preferred embodiment of a multi-component application system with a mixing device the two pastes are each filled into a chamber of a conventional double chamber syringe and closed. In case of an invasive medical application they are sterilized in this form. For use, the double chamber syringe is connected to a static mixer and dispensed and mixed either manually, by means of a geared hand device (pistol) or by means of a foreign-driven device. This mixing action of the two components starts the curing reaction. The corresponding double chamber syringes and static mixers are in principle known (e.g. as products of the company Mixpac) but are for the first time described here for the application of the products according to the invention. In a further, also especially preferred, embodiment of the invention as a single component application system the implant material is comprised only of one component that contains all substances required for initiating a curing reaction with the exception of water (optionally containing further excipients and active ingredients) and in which upon introduction into an aqueous medium and/or contact with water-containing surfaces spontaneously a curing reaction is started. Typically, the implant material in this embodiment contains (organo) mineral powder, surface-active agent(s) and optionally further excipients and active ingredients combined in a paste. This paste can be mixed with water according to the invention in analogy to the afore described methods. The special feature of this application form resides however in the fact that the paste, comprised of a single component, without further admixture can be introduced into an aqueous environment and by taking up water from the environment or exchange of organic liquid (oil) for water, cure to a solid material.

Advantageously, the implant material according to the invention in this embodiment can be embodied as a simple cartridge, e.g. as a syringe, and thus can function as a very simple embodiment that is user-friendly. Especially suitable is this embodiment for applications of the implant materials according to the invention in a relatively thin layer that has on all sides contact with aqueous surfaces or liquids or in which the material has available a longer period of time for a complete curing action. This formulation is especially advantageous for use as an organo-mineral adhesive for moist material surfaces and in particular for gluing bone structures.

The implant materials according to the invention can be used for many technical, medical (medical-engineering) and/or pharmaceutical applications in a useful way. The illustrated aspects of the invention make the implant materials especially suitable for producing medical products and pharmaceutical products and here in particular for the manufacture of bone cements, bone replacement materials, bone adhesives, tooth filling materials and/or implantable active ingredient carriers. Claimed among them are especially embodiments of the invention as a single or two-component system comprised completely of biocompatible materials that are offered in sterilized form and cure within the body.

As a result of these advantages, the use of the implant materials of the present invention for producing bone replacement material, bone cements, bone adhesives and implantable active ingredient carriers is especially preferred. Bone cements are embodied in accordance with the implant material of the present invention and are matched to the specific applications. Bone replacement materials are compositions of the implant material according to the invention, e.g. for filling in bone defects. In this case, it may be advantageous to form the bone replacement material from the implant material according to the invention before implantation into the body in the form of a cured solid material and to subsequently introduce/implanted it in the bone defect.

Bone adhesives are preparations of the implant material according to the invention, e.g. for connecting and attaching bone fragments after bone fractures or for attaching e.g. metallic or ceramic or polymeric implant materials on or in the bone. In this function, the bone adhesives contain, in addition to the implant materials of the present invention, substances that enhance adhesion that are, for example, known from the field of dentistry as adhesion promoters and/or substances such as polyacrylates and/or polymers produced from anionic monomers and/or copolymers. These substances are used in the field of dentistry inter alia for improved adhesion of filling materials to the tooth substance (that has a great similarity to bone substance). With the implant materials according to the invention they are combinable in advantageous and versatile ways because they can be combined with the paste as well as with the aqueous solution in wide concentration ranges. This differentiates the implant materials according to the invention from conventional preparations because in particular the charged or strongly polar adhesion promoters that in this respect are especially effective cannot be combined easily with conventional mineral cements. The addition of the adhesion promoters effects a greater adhesion of the implant material on the bone tissue. Active ingredient carriers are preparations of the implant materials according to the present invention that contain pharmacologically active ingredients in concentrations that effect a therapeutic function in the human or animal organism. These active ingredients are released after implantation from the implant material. Preferred is therefore the combination with active ingredients that develop a direct local action that thus act directly on the tissue in the surroundings of the implant material. Preferred is the combination with active ingredients that stimulate the bone metabolism and counteract local inflammations. Especially preferred are active ingredient carriers on the basis of the implant materials according to the invention that contain antimicrobial active ingredients such as antibiotics, bone-anabolic proteins and/or peptides such as bone morphogenetic proteins (BMPs) or peptides derived from parathormone or inhibiting substances of bone resorption such as bisphosphonates or proton pump inhibitors.

An especially preferred application of the polymer systems according to the invention resides in filling of bone defects and in augmentation of osteoporotic bone. In most cases, this application is carried out by minimal-invasive surgery technique.

A typical example for this are the different methods of vertebroplasty that in the past years have become more and more popular and whose clinical effectiveness is being documented better and better. It is therefore to be expected that these treatment technologies will be further expanded on and the treated cases will increase greatly. The further development of the methods of vertebroplasty (including the so-called kyphoplasty) are especially importantly dependent on the availability of improved augmentation materials. The known bone cements are only suitable to a limited extent; even when some products are offered especially for vertebroplasty they are still conventional bone cements with minimally modified viscosity, cuing kinetics and increased contents of x-ray contrast material. The implant materials according to the invention are in principle superior in these applications because they are significantly simpler to manipulate. For the successful clinical application they must be combined with suitable application systems for introduction of the implant material into the bone. For this purpose, in the simplest case simple syringe system can be employed as they are still used today in vertebroplasty. More expedient is however mixing of the implant material in the double chamber syringe and a static mixer and the combination with an injection cannula or a suitable tube that extends to the implant location. It is in particular advantageous that the implant material is first mixed when extrusion takes place, i.e., in a simple way with a cement cartridge several injections can be done and no temporally matched preparatory work is required because the polymer system is immediately ready for use when exiting from the syringe. As a single component system the implant material can even be applied to the bone without requiring any prior mixing. With respect to the prior art that has been discussed in the introductory section this is a significant advantage in regard to application technology, and training of the surgery personnel regarding preparation of the implant material is obsolete.

An especially preferred application is the method known as kyphoplasty in which first the osteoporotic bone of the vertebra is expanded by means of a balloon and is compressed within the surroundings and, subsequently, into the produced cavity a bone cement is introduced. Especially in this application, the combination of the application instruments with the implant material according to the invention is especially advantageous because in this case an advantageous application system can be combined with an advantageous filling material. Therefore, all combinations of the implant material according to the invention with application systems that are suitable to introduce in a minimally invasive way the implant material according to the invention into bone defects, fracture gaps, osteoporotic bone, bone tumors or bone structures rarified in other ways, are claimed. Also, all attachments are claimed that may be attached to a mixing system of the type of the aforementioned double chamber syringes or can be connected thereto for this purpose in order to apply with the aid thereof the implant materials according to the invention at the target location.

The implant materials according to the present invention can be manipulated in an especially advantageous way intraoperatively, i.e., prepared for the introduction into the body. This differentiates them basically from conventional bone cements that are mixed from powder and liquid. At the same time, the material properties enable the simple and reliable minimal-invasive application by means of a cannula. The free combination possibilities of the first and the second components of the implant material within a very wide mixing ratio (e.g. 1:1, 1:2, 1:4, 1:10) enable also the combination of the implant material with various biological factors that may be or should be added first at the implantation location. This applies in particular to serum components such as plasma rich in platelets, intraoperatively obtained cell suspensions and suspensions that have been harvested by prior culturing.

DESCRIPTION OF PREFERRED EMBODIMENTS

Examples

Based on the following examples the invention will be explained in more detail:

Example 1: Calcium Phosphate Cement CPC as Two-Component System

First Component

The employed CPC is comprised of 60% by weight α-TCP, 26% by weight CaHPO4, 10% by weight CaCO3 and 4% by weight precipitated hydroxyl apatite. The powders that have been comminuted beforehand are mixed in a ball mill and intensively ground.

100 g of the powder component of the CPC are mixed with 20 ml Miglyol 812 in a planetary ball mill (Fritsch Pulverisette 6) in a 500 ml beaker with 50 balls (10 mm diameter, each made of zirconium dioxide) for 3×15 min. (30 min. interruption, respectively) at a speed of 500 rpm. The result is a homogenous viscous paste with the consistency of peanut butter.

2nd Component

As a water-containing carrier liquid 6% hydroxy ethyl starch, 5% Tween 80 and 4% $Na_2HPO_4$ are combined in water.

With the two components the following tests are performed:

a) As a cement mixture according to the invention 10 g of the paste with 2 ml of the aqueous solution are placed into a beaker and mixed with a spatula. Paste and aqueous liquid can be levigated homogeneously within a short period of time wherein the viscosity of the mixture increases slowly. Approximately 3 min after start of the mixing action, the paste begins to solidify and reaches an initial strength. After 6 hours the formulation according to the invention has a compression strength of approximately 12 MPa, after 3 days the compression strength is 15 MPa.

b) The test under a) is repeated after storage of the paste for 6 months under normal conditions. The paste was stored for this purpose in a simple screw-lid glass without further measures. The mixing behavior shows no recognizable differences to the tests under a). The compression strength after 6 hours is 12 MPa, after 3 days 15 MPa.

c) The test under a) is repeated with 10 g of the paste and 2.5 ml of the aqueous solution With the greater quantity of aqueous solution it takes somewhat longer until paste and solution are distributed homogeneously. Otherwise no recognizable differences between the two versions is noted. The initial strength is also reached after 3 min. The compression strength after 6 hours is 10 MPa, after 3 days 14 MPa.

d) The test under c) is repeated with a conventional double chamber syringe of the company Mixpac (volume: 10 ml; ratio of cartridges: 4:1). After a minimal inhomogeneity at the beginning of the dispensing action the further dispensed strand is homogeneous and cures as in the manually mixed sample in appr. 3 min.

In example 1 with respect to use of the cement in a two-chamber injection syringe (Mixpac) a very short curing time was selected because in this case the cement can be applied directly to the implant location. For an open mixing action in a mixing beaker the initial curing time can be adjusted to a value of appr. 5-7 min in that the concentration of Na2HPO4 solution is reduced to 1.0%. Surprisingly and notably in this connection is also the fact that the calcium phosphate cement according to example 1 cures faster than the corresponding conventional calcium phosphate cement. The results thus show that with the novel formulation cements are obtained that react to a solid material. The obtained strength values of the solid materials are approximately 30-40% lower than in conventional counterparts made from powder and mixing liquid. However, upon further optimization significantly higher strength values are to be expected (the conventional base cement is also the result of extensive optimization work) and, moreover, the measured values are at or above the level of spongious bone and therefore the tested formulations are already suitable for clinical use in many indications, in particular in those in which the mechanical properties of the bone replacement material are not decisive—which is the case in most situations.

Example 2: Calcium Phosphate Cement as Single Component System 20 g CPC cement powder according to example 1 are manually premixed with 4 ml Miglyol 812, 300 mg $Na_2HPO_4$, 500 mg Tween 80, and 200 mg Amphisol A and subsequently mixed in a 100 ml beaker with 10 balls of 10 mm diameter (zirconium dioxide embodiment) 3×15 min with 30 min interruption inbetween at 500 rpm. The result is a homogeneous viscous paste. The paste is filled into a 10 ml syringe and subsequently injected into a beaker with simulated body fluid (SBF) (without cannula). The extruded strand remains completely intact even when lightly shaken and cures in less than 60 min to such an extent that it can be removed from the liquid without falling apart. The liquid remains completely clear which indicates that no cement particles are washed out. The final strength is reached as in conventionally mixed powder+liquid after appr. 24 hours.

Example 3, Single Component Cements

Single component cements according to the following formulation have been formulated in accordance with example 2 and tested in that the obtained respective pastes are filled into a 6×6×2 mm mold and introduced into simulated body fluid for curing. The compression strength was determined in a universal testing machine after 100 hours of incubation time. The determination of the curing time was done according to ASTM 266C. The consistency of the paste was adjusted to a value comparable to that of peanut butter at room temperature.

| Single component cements | | | | | | |
|---|---|---|---|---|---|---|
| type | cement powder | oil | Tween | Amphisol | accelerator/ reactant | compression strength | curing time |
| CPC | 80% | 15% | 3% | 1% | 1% Na2HPO4 | 14 MPa | 5 min |
| MgPC *) | 74% | 13% | 0.8% | 2% | 10% (NH4)2HPO4 | 13 MPa | 5 min |

CPC: calcium phosphate cement according to example 1
MgPC: magnesium phosphate cement; the manufacture of the MgPC cement powder was carried out by sintering at 1,100° C. for 3 hours from MgHPO$_4$ and Mg(OH)$_2$ in a ratio (2:1), leading to a molar composition of Mg$_3$(PO$_4$)$_2$. After sintering, the cement powder was ground in a ball mill for 4 hours to an average particle size of <25 μm. Amphisol: surface-active agent.
+) magnesium phosphate cement cures by reaction with ammonium salts; in this example with diammonium hydrogen phosphate ((NH$_4$)2HPO$_4$), 10% (NH$_4$)2HPO$_4$ are therefore to be added to the cement powder so that a total powder quantity of 84% results.

As an oil Miglyol 812 was used.

The list of cement formulations shows that the inventive principle of use of anhydrous liquids that in the chemical sense are not miscible with water as carrier liquids for mineral hydraulic bone cements is very versatile, universally applicable and profitable.

Example 4, Additional Two-Component Cements

Two component cements according to the following formulation have been formulated and tested in accordance with example 1b.

| Two-paste cements (2-component cements) | | | | | | | |
|---|---|---|---|---|---|---|---|
| type | cement powder | oil | Tween | Amphisol | accelerator/ paste 2 | compression strength | curing time |
| CPC | 80% | 17% | 2% | 1% | 100% water | 14 MPa | 8 min |
| MgPC *) | 75% | 13% | 0.8% | 0.8% | 10% (NH4)2HPO4 in paste 1; paste 2: 28% (NH4)2HPO4, 3% CMS, 1% Span, 68% water | 23 MPa | 5 min |
| brushite cement | 81% | 17% | 1% | 1% | paste 2: 4% Na2HPO4, 3% CMS, 1% Span, 92% water | 4.5 MPa | 6 min |
| HA cement | 81% | 17% | 1% | 1% | paste 2: 4% Na2HPO4, 3% CMS, 1% Span, 92% water | 6.4 MPa | 12 min |

CMS: carboxymethyl starch
Span: surface-active agent
*) the total quantity of cement powder is in this embodiment 85% because the anhydrous paste contains 10% (NH$_4$)2HPO$_4$ as a solid and additionally a portion of this ammonium salt is dissolved in the aqueous mixing solution.
Brushite cement: cement powder according to Pittet C, Lemaitre J. Mechanical characterization of brushite cements: A Mohr circles' approach, J Biomed Mater Res 2000; 53 (6) 769-780
HA cement: cement powder according to Brown W E, Chow L C. A new calcium phosphate water setting cement. In: Brown P W, editor. Cements research progress. Westerville, OH: American Ceramic Society; 1986. p. 352-79.

All solids-containing pastes (paste 1, respectively) were adjusted by appropriate adjustment of the quantity ratios of powder and oil to a consistency of peanut butter at room temperature.

The illustrated results are measured values of applicability tests. It is to be assumed that with all tested cement types upon further optimization work significant increases in the strength values will be achieved. The tested MgCaP cements exhibit excellent mechanical properties already after initial experiments. The curing times for the carried-out experiments are already within the range of known corresponding powder-liquid variants.

ABBREVIATIONS

ACP amorphous calcium phosphate
CdHA calcium-deficient hydroxyl apatite
CP calcium phosphate
CPC calcium phosphate cement
DCPA dicalcium phosphate anhydrite
DCPD dicalcium phosphate dihydrate
HA hydroxyl apatite
Miglyol 812 saturated triglyceride with fatty acids of the chain lengths of 8-12
MCPA monocalcium phosphate anhydrite
MCPM monocalcium phosphate monohydrate
OCP octacalcium phosphate
SDS sodium dodecyl sulphate
TCP tricalcium phosphate
TTCP tetracalcium phosphate

What is claimed is:

1. Paste, suspension or dispersion for producing an implant material on the basis of a hydraulic cement, the paste, suspension or dispersion containing a powdery solid containing calcium and/or magnesium compounds, wherein the solids to >75% are comprised of calcium and/or magnesium salts and/or oxides and/or hydroxides of calcium and/or magnesium, that, upon mixing with an aqueous liquid or after introduction into an aqueous liquid, cures to a solid body,
wherein the paste, suspension or dispersion further contains a hydrophobic carrier liquid in a quantity of 10% by weight to 50% by weight of a total weight of the paste, suspension or dispersion, wherein the hydrophobic carrier liquid is characterized by not being soluble in water or by being only soluble in water to less than 25% by volume and characterized by water not being soluble or by being only soluble to less than 25% by volume in the carrier liquid, said hydrophobic carrier liquid being medium-chain triglycerides,
wherein the paste, suspension or dispersion contains a surface active agent comprising cetyl phosphate, and
wherein the paste, suspension or dispersion under normal conditions of 25 degrees Celsius and 101.3 kPa has a liquid to pasty consistency and is free of water.

2. Paste, suspension or dispersion according to claim 1, characterized in that the powdery solid is suspended/dispersed as a fine powder and in that at least 10% of the powdery solid has a particle size <10 μm and in that at least 10% of the powdery solid has a particle size of >50 μm.

3. Paste, suspension or dispersion according to claim 1, characterized in that the solids to >30% are comprised of salts of silicic acid or its condensates and/or salts of phosphoric acid or its condensates and/or salts of the glycerine phosphoric acid and/or salts of sulfuric acid and/or salts of carbonic acid.

4. Paste, suspension or dispersion according to claim 3, characterized in that the solids are comprised to >50% of calcium and/or magnesium phosphates.

5. Paste, suspension or dispersion according to claim 3, characterized in that the calcium compounds are selected from monocalcium phosphate monohydrate (MCPM), monocalcium phosphate anhydrite (MCPA), dicalcium phosphate anhydrite (DCPA), dicalcium phosphate dihydrate (DCPD), octacalcium phosphate (OCP), α-tricalcium phosphate (α-TCP), β-tricalcium phosphate (β-TCP), amorphous calcium phosphate (ACP), hydroxyl apatite (HA), calcium-deficient hydroxyl apatite (CdHA), substituted hydroxyl apatite, non-stoichiometric hydroxyl apatite, nano hydroxyl apatite, tetracalcium phosphate (TTCP), calcium sulfate ($CaSO_4$), calcium sulfate hemihydrate ($CaSO_4 \times 0.5\ H_2O$), calcium sulfate dihydrate ($CaSO_4 \times 2\ H_2O$), calciumoxide (CaO), calcium hydroxide ($Ca(OH)_2$), calcium carbonate ($CaCO_3$), calcium glycerophosphate, calcium citrate, calcium lactate, calcium acetate, calcium tartrate, calcium chloride ($CaCl_2$), calcium silicates and their mixtures with one another.

6. Paste, suspension or dispersion according to claim 3, characterized in that the magnesium compounds are selected from magnesium hydrogen phosphate ($MgHPO_4$) in the form of the hydrates and as anhydrous substance, trimagnesium phosphate ($Mg_3(PO_4)_2$), magnesium dihydrogen phosphate ($Mg(H_2PO_4)_2$) in the form of the hydrates and as anhydrous substance, magnesium chloride ($MgCl_2$) in the form of the hydrates and as anhydrous substance, magnesium glycerophosphate, magnesium hydroxide ($Mg(OH)_2$), magnesium hydroxide carbonate, magnesium oxide (MgO), magnesium citrate, calcium magnesium carbonate ($CaMg(CO_3)_2$, dolomite) and their mixtures with one another.

7. Paste, suspension or dispersion according to claim 3, characterized in that the solids to >25% contain α- or β-tricalcium phosphate, tetracalcium phosphate, dicalcium phosphate anhydrite or amorphous calcium phosphate.

8. Paste, suspension or dispersion according to claim 3, characterized in that the solids moreover contain ammonium salts that with one of the magnesium compounds cure to a magnesium ammonium phosphate solid material.

9. Paste, suspension or dispersion according to claim 3, characterized in that the solids contain to >5% calcium or magnesium hydrogen phosphate as hydrate or anhydrous substance.

10. Paste, suspension or dispersion according to claim 3, characterized in that the solids contain >10% calcium sulfate.

11. Paste, suspension or dispersion according to claim 1, characterized in that the at least one component contains a mineral powder mixture that in combination with the aqueous solution has a molar calcium/phosphate ratio of >1.35.

12. Paste, suspension or dispersion according to claim 1, characterized in that the at least one component contains a mineral powder mixture that in combination with the aqueous solution has a molar calcium/phosphate ratio of 0.9-1.35.

13. Paste, suspension or dispersion according to claim 1, characterized in that the powdery solid is either partially or completely dispersed in the carrier liquid and that the carrier liquid itself is soluble to less than 25% in water.

14. Paste, suspension or dispersion according to claim 1, characterized in that the carrier liquid contains dissolved, suspended or dispersed solids or one or more liquids that have a solubility in water of more than 1% (w/w), wherein the carrier liquid is swellable or miscible with water.

15. Paste, suspension or dispersion according to claim 1, characterized in that the carrier liquid is miscible with water or the carrier liquid is miscible with aqueous solutions that are stabilized by an emulsifier.

16. Paste, suspension or dispersion according to claim 1, characterized in that the carrier liquid comprises two or more substances wherein each of the substances are present in the carrier liquid in at least 0.1%.

17. Paste, suspension or dispersion according to claim 1, characterized in that from about 25% to about 75% by weight of the paste, suspension or dispersion comprises dispersed solids.

18. Paste, suspension or dispersion according to claim 1, characterized in that the paste, suspension or dispersion contains >70% of dispersed solids.

19. Paste, suspension or dispersion according to claim 1, characterized in that the paste, suspension or dispersion contains, in addition to suspended/dispersed solids and the carrier liquid, said one or several surface-active agents and/or highly dispersed solids, dissolved or suspended polymers with a molecular weight of >2,500.

20. Paste, suspension or dispersion according to claim 1, characterized in that the paste, suspension or dispersion further contains one or more dissolved or suspended pharmacological active ingredients.

21. Multi-component application system with a mixing device, comprising the paste, suspension or dispersion according to claim 1.

22. Single component application system containing the paste, suspension or dispersion according to claim 1, wherein the paste, suspension or dispersion contains all substances required for triggering a curing reaction with the exception of water and upon introduction of the paste, suspension or dispersion into an aqueous medium and/or contact with water-containing surfaces a curing reaction of the paste, suspension or dispersion is spontaneously triggered.

23. Paste, suspension or dispersion according to claim 1 in the form of bone cements, bone replacement materials, bone adhesives, tooth filling materials and/or implantable active ingredient carriers.

24. Paste, suspension or dispersion according to claim 1 in combination with application systems for augmenting osteoporotic or other pathologically modified bone areas and for filling bone defects of all kinds.

25. Paste, suspension or dispersion according to claim 1, characterized in that the powdery solid contains 60% by weight of tricalcium phosphate, 26% by weight $CaHPO_4$, 10% by weight $CaCO_3$, and 4% by weight precipitated hydroxyl apatite.

* * * * *